US010750969B2

(12) United States Patent
Matsuura et al.

(10) Patent No.: US 10,750,969 B2
(45) Date of Patent: Aug. 25, 2020

(54) HEARTBEAT DETECTION METHOD AND HEARTBEAT DETECTION DEVICE

(71) Applicant: NIPPON TELEGRAPH AND TELEPHONE CORPORATION, Tokyo (JP)

(72) Inventors: Nobuaki Matsuura, Tokyo (JP); Kei Kuwabara, Tokyo (JP); Kazuhiko Takagahara, Tokyo (JP); Ryusuke Kawano, Tokyo (JP); Hiroshi Koizumi, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 0 days.

(21) Appl. No.: 15/509,726

(22) PCT Filed: Aug. 28, 2015

(86) PCT No.: PCT/JP2015/074406
§ 371 (c)(1),
(2) Date: Mar. 8, 2017

(87) PCT Pub. No.: WO2016/039182
PCT Pub. Date: Mar. 17, 2016

(65) Prior Publication Data
US 2017/0258351 A1    Sep. 14, 2017

(30) Foreign Application Priority Data
Sep. 9, 2014   (JP) ................................. 2014-183013

(51) Int. Cl.
*A61B 5/04*   (2006.01)
*A61B 5/0456*   (2006.01)
(Continued)

(52) U.S. Cl.
CPC .......... *A61B 5/0456* (2013.01); *A61B 5/0245* (2013.01); *A61B 5/04012* (2013.01); *A61B 5/7207* (2013.01); *A61B 5/7239* (2013.01)

(58) Field of Classification Search
CPC .. A61B 5/0456; A61B 5/04012; A61B 5/0245
See application file for complete search history.

(56) References Cited

U.S. PATENT DOCUMENTS

2005/0113703 A1    5/2005 Farringdon et al.
2006/0287606 A1*  12/2006 Hong ...................... A61B 5/024
                                                    600/528

(Continued)

FOREIGN PATENT DOCUMENTS

CA    2538710 A1    3/2005
CN    1113739 A    12/1995
(Continued)

OTHER PUBLICATIONS

"ECG Implementation on the TMS320C5515 DSP Medical Development Kit (MDK) with the ADS1298 ECG-FE", Texas Instruments Incorporated, <http://www.ti.com/lit/an/sprabj1/sprabj1.pdf>, 2011.

(Continued)

*Primary Examiner* — Rex R Holmes
(74) *Attorney, Agent, or Firm* — Womble Bond Dickinson (US) LLP

(57) ABSTRACT

A heartbeat detection device includes a peak search unit (4) for searching for one of a peak at which a value M obtained from a sampling data sequence of an electrocardiographic waveform of a living body changes from an increase to a decrease and a peak at which the value M changes from a decrease to an increase, and a heartbeat time determination unit (5) for checking the value M in a predetermined time domain before a time of the peak and the value M in a predetermined time domain after the time of the peak, and (Continued)

setting the time of the peak as a heartbeat time if differences between the value M at the time of the peak and the values M in the predetermined time domains are not smaller than a predetermined amount.

16 Claims, 13 Drawing Sheets

(51) Int. Cl.
*A61B 5/00* (2006.01)
*A61B 5/0245* (2006.01)

(56) References Cited

U.S. PATENT DOCUMENTS

| | | |
|---|---|---|
| 2009/0156948 A1 | 6/2009 | Shimizu et al. |
| 2013/0267859 A1 | 10/2013 | Okuda et al. |
| 2015/0366473 A1 | 12/2015 | Shimuta et al. |

FOREIGN PATENT DOCUMENTS

| | | |
|---|---|---|
| CN | 101272731 A | 9/2008 |
| CN | 101953682 A | 1/2011 |
| CN | 101991410 A | 3/2011 |
| CN | 103153177 A | 6/2013 |
| CN | 103690156 A | 4/2014 |
| CN | 105007809 A | 10/2015 |
| EP | 2319410 A1 | 5/2011 |
| EP | 2628444 A1 | 8/2013 |
| JP | 2002-078695 A | 3/2002 |
| JP | 2003-000561 A | 1/2003 |
| JP | 2003-339651 A | 12/2003 |
| JP | 2007-504917 A | 3/2007 |
| JP | 2012-101027 A | 5/2012 |
| KR | 10-2006-0129178 A | 12/2006 |
| WO | 2005/027720 A2 | 3/2005 |
| WO | WO 2012/049903 A1 | 4/2012 |
| WO | WO 2014/132713 A1 | 9/2014 |

OTHER PUBLICATIONS

Office Action received for Chinese Patent Application No. 201580047949.X, dated Jan. 30, 2019, 17 pages (8 pages of English Translation and 9 pages of Office Action).

International Search Report and Written Opinion received for PCT Patent Application No. PCT/JP2015/074406, dated Dec. 1, 2015, 14 pages (7 pages of English Translation and 7 pages of Original Document).

International Preliminary Report on Patentability received for PCT Patent Application No. PCT/JP2015/074406, dated Mar. 23, 2017, 12 pages (7 pages of English Translation and 5 pages of Original Document).

Office Action received for Chinese Patent Application No. 201580047949.X, dated Nov. 28, 2019, 21 pages (12 pages of English Translation and 9 pages of Office Action).

Office Action received for Chinese Patent Application No. 201580047949.X, dated Aug. 12, 2019, 8 pages (4 pages of English Translation and 4 pages of Office Action).

Office Action received for Chinese Patent Application No. 201580047949.X, dated May 6, 2020, 30 pages (16 pages of English Translation and 14 pages of Office Action).

Yurun, Ma, "The Research of ECG Signal Preprocessing and QRS Complex Detection Techniques", Chinese Master's Theses Full-text Database Information Science and Technology, No. 11, Nov. 15, 2013, pp. 36-40 (Original Document Only).

\* cited by examiner

HEARTBEAT DETECTION METHOD AND HEARTBEAT DETECTION DEVICE

The present application is a U.S. National Stage application of International application No. PCT/JP2015/074406 filed on Aug. 28, 2015, which claims priority to Japanese Application No. 2014-183013 filed on Sep. 9, 2014, all of which are incorporated herein by reference.

TECHNICAL FIELD

The present invention relates to a heartbeat detection method and heartbeat detection device for extracting biological information such as a heartbeat interval (R-R interval) from an electrocardiographic waveform.

BACKGROUND ART

An ECG (Electrocardiogram) waveform is obtained by observing and recording the electrical activity of a heart, and is measured by attaching electrodes to a body surface in a general method. As an ECG waveform lead system, that is, an electrode arrangement, there are various types using limbs and chest. In the V3 to V5 leads among precordial leads, an electrode is arranged at the left chest. In the CC5 lead suitable for monitoring an ECG waveform for a long time, electrodes are arranged at the symmetrical positions of left and right chests. These leads have the advantage that a stable waveform having a large amplitude is obtained.

FIG. 11 shows an example of an ECG waveform. In FIG. 11, the ordinate represents the electric potential and the abscissa represents the time. The ECG waveform is formed from continuous heartbeat waveforms, and one heartbeat waveform is formed from components such as P, Q, R, S, and T waves reflecting the activities of atriums and ventricles.

It is known that biological information such as an R-R interval obtained from an ECG waveform is an index reflecting the autonomic activity. It is useful for evaluation of the autonomic function to obtain an ECG waveform in daily life and analyze data of a heartbeat fluctuation from detected heartbeats. Furthermore, there is an application in which an exercise tolerance is estimated from heartbeat data during an exercise, and used for optimization or the like.

As a conventional heartbeat detection method, the following literatures are known. Japanese Patent Laid-Open No. 2002-78695 discloses an arrangement for removing the fluctuation of the baseline of an ECG waveform. In addition, Japanese Patent Laid-Open No. 2003-561 discloses an arrangement of recognizing an R wave using a threshold based on an amplitude between the peak and valley of a waveform.

A method of obtaining the R-R interval or the like based on a change in value obtained by calculating the first derivative of an ECG waveform is described in "ECG Implementation on the TMS320C5515 DSP Medical Development Kit (MDK) with the ADS1298 ECG-FE", Texas Instruments Incorporated, <http://www.ti.com/lit/an/sprabj1/sprabj1.pdf>, 2011. More specifically, the absolute value of the difference between the (n+1)th sampling value and the (n−1)th sampling value is obtained, peaks are detected based on a threshold, and then the time width between two peaks is set as the R-R interval.

DISCLOSURE OF INVENTION

Problem to be Solved by the Invention

However, the above-described heartbeat detection method has the following problem. That is, if heartbeat data in daily life or during an exercise is to be recorded or analyzed, noise caused by a body motion or the like may be mixed into an ECG waveform, unlike measurement in a rest state.

FIGS. 12 and 13 show graphs for explaining the conventional problem, in which the abscissa represents the time [ms] and the ordinate represents the electric potential [arbitrary unit] replaced by a digital value. FIG. 12 shows an example of sampling data of an ECG waveform, and R in FIG. 12 represents an R wave to be detected as a heartbeat. Noise is superimposed in a short cycle around 189,000 ms in FIG. 12. Even if an attempt is made to detect a heartbeat based on a threshold from such ECG waveform, the peak of the R wave and that of the noise are at the same level, and it is thus difficult to identify and extract only a heartbeat.

On the other hand, there is also provided a method of detecting a heartbeat based on the derivative of an ECG waveform. In general, an ECG waveform is processed as a discrete data sequence in data processing. Therefore, obtaining the derivative of an ECG waveform is equivalent to obtaining the time subtraction of the ECG waveform. FIG. 13 shows a waveform obtained by calculating the time subtraction of the ECG waveform shown in FIG. 12. FIG. 13 is a graph obtained by plotting, at each time of the sampling data of the ECG waveform, a value obtained by subtracting a value 5 ms before from a value 5 ms after, that is, a first derivative. In FIG. 13, D represents a peak to be detected as a heartbeat. In a usual ECG waveform, an abrupt change from the R wave to the S wave can be made conspicuous by obtaining the first derivative, thereby facilitating detection of a heartbeat. In FIG. 13, however, noise components having almost the same level as that of the peaks D each caused by an abrupt change from the R wave to the S wave are included, and it is thus difficult to extract heartbeats based on the threshold.

The present invention has been made to solve the above-described problem, and has as its object to provide a heartbeat detection method and heartbeat detection device, which can appropriately detect a heartbeat and its time from data in which noise is superimposed on an ECG waveform.

Means of Solution to the Problem

According to the present invention, there is provided a heartbeat detection method comprising a peak search step of searching for one of a peak at which a value M obtained from a sampling data sequence of an electrocardiographic waveform of a living body changes from an increase to a decrease and a peak at which the value M changes from a decrease to an increase, and a heartbeat time determination step of checking, among the values M obtained from the sampling data sequence, the value M in a predetermined time domain before a time of the peak and the value M in a predetermined time domain after the time of the peak, and setting the time of the peak as a heartbeat time if differences between the value M at the time of the peak and the values M in the predetermined time domains are not smaller than a predetermined amount.

According to the present invention, there is also provided a heartbeat detection device comprising peak search means for searching for one of a peak at which a value M obtained from a sampling data sequence of an electrocardiographic waveform of a living body changes from an increase to a decrease and a peak at which the value M changes from a decrease to an increase, and heartbeat time determination means for checking, among the values M obtained from the sampling data sequence, the value M in a predetermined time domain before a time of the peak and the value M in a predetermined time domain after the time of the peak, and setting the time of the peak as a heartbeat time if differences between the value M at the time of the peak and the values M in the predetermined time domains are not smaller than a predetermined amount.

Effect of the Invention

According to the present invention, it is possible to appropriately detect a heartbeat even from a sampling data sequence including noise by searching for a peak at which a value M obtained from the sampling data sequence of an electrocardiographic waveform of a living body changes from an increase to a decrease or from a decrease to an increase, checking the value M in a predetermined time domain before a time of the peak and the value M in a predetermined time domain after the time of the peak, and setting the time of the peak as a heartbeat time if the difference between the value M at the time of the peak and the values M in the predetermined time domains is equal to or larger than a predetermined amount. In addition, according to the present invention, since a peak derived from a heartbeat is detected without using the threshold, even if the level of the target electrocardiographic waveform changes, it is possible to appropriately detect a heartbeat without any influence of the change.

BEST MODE FOR CARRYING OUT THE INVENTION

[Principle of Invention]

Figure 1:
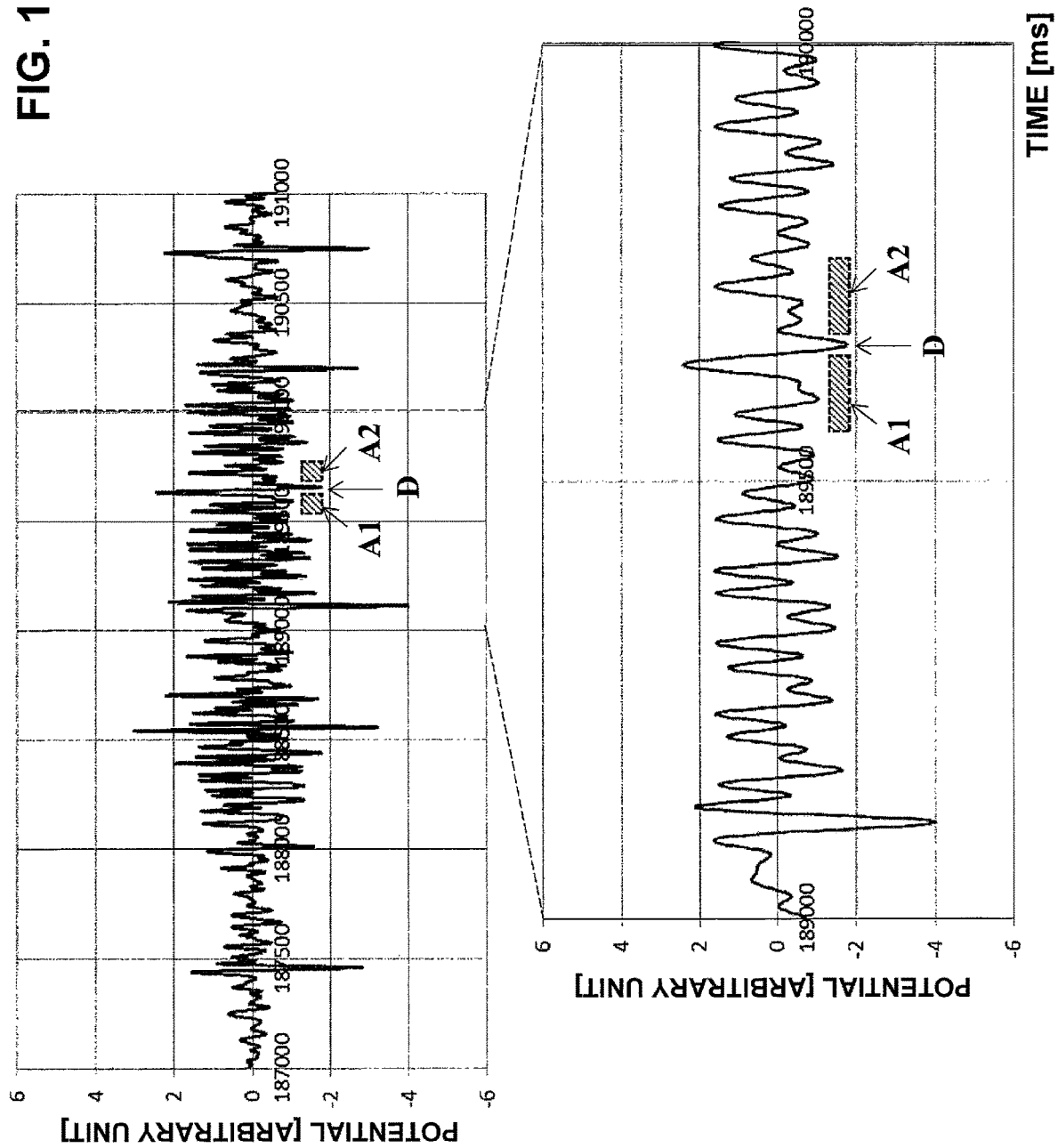
FIG. 1 is a graph for explaining a principle according to the present invention.
Figure 13:
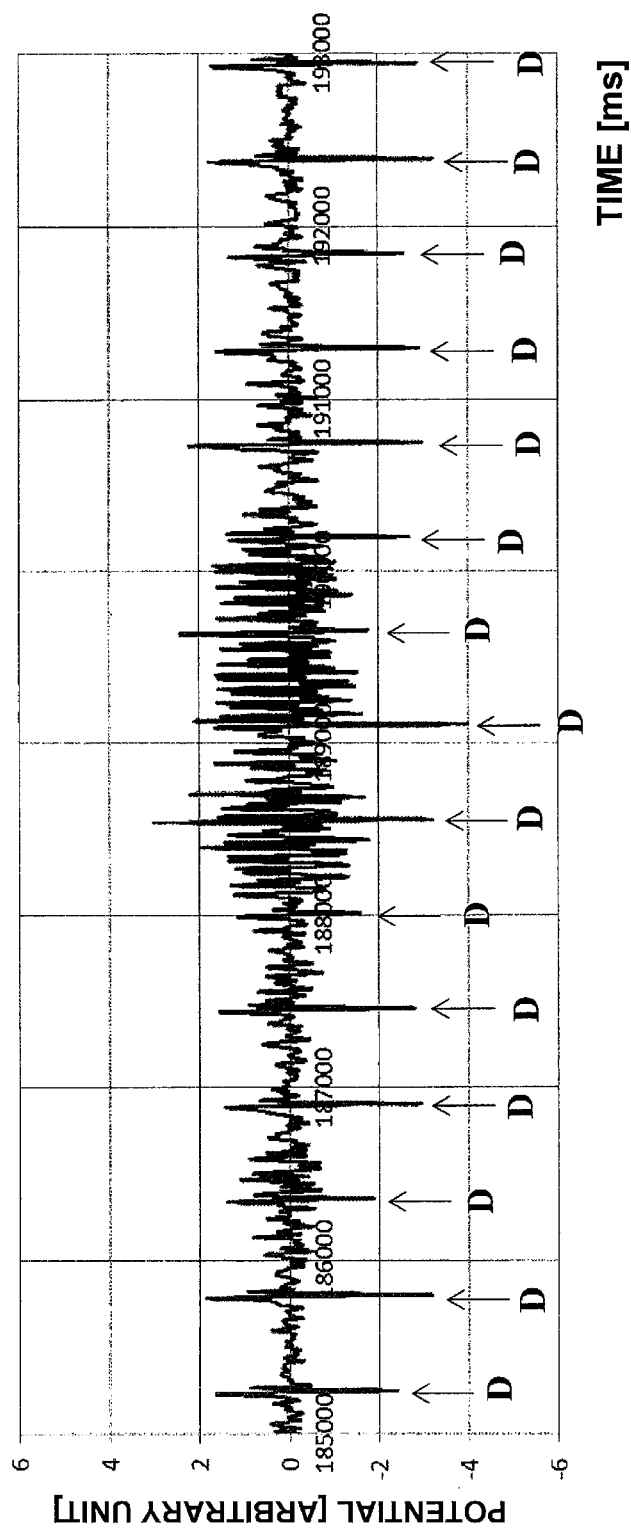
FIG. 13 is a graph for explaining the conventional problem.

FIG. 1 is a graph for explaining a principle according to the present invention. In FIG. 1, the abscissa represents the time [ms] and the ordinate represents the electric potential [arbitrary unit] replaced by a digital value. A waveform shown in FIG. 1 is obtained by plotting the amount of change (first derivative value) of sampling data. Among two waveforms shown in FIG. 1, a waveform on the upper side is obtained by enlarging a portion in FIG. 13, and a waveform on the lower side is obtained by further enlarging a period of 189,000 ms to 190,000 ms in FIG. 13.

Referring to FIG. 1, there is a peak D considered to be caused by a heartbeat around 189,700 ms. However, since the peak D is surrounded by noise and the level of the noise is almost equal to that of the peak D, it is difficult to detect the peak D based on a threshold. On the other hand, the reason why the peak D is considered to be caused by a heartbeat is that the peak D protrudes more than other components around it.

It is possible to detect the peak D by, for example, checking a value in a time range A1 of −100 ms to −15 ms and a value in a time range A2 of +15 ms to +100 ms with respect to time K at which the amount of change of the sampling data of the ECG waveform changes from a decrease to an increase, and imposing the condition that the values in the ranges A1 and A2 are larger than a value at time K by 0.5 or more. Since this condition is satisfied by peaks caused by other heartbeats, these peaks can be detected by the same series of procedures.

As described above, according to the present invention, let M be a value obtained from the sampling data sequence of the ECG waveform. With respect to time T of a peak at which the value M changes from an increase to a decrease or from a decrease to an increase, the value M in a predetermined time domain of $(T-\Delta t2)$ to $(T-\Delta t1)$ before time T of the peak and the value M in a predetermined time domain of $(T+\Delta t1)$ to $(T+\Delta t2)$ after time T of the peak are checked ($\Delta t2 > \Delta t1$). If the differences between the value M at time T of the peak and the values M in the predetermined time domains are equal to or larger than a predetermined amount y, time T of the peak is set as a heartbeat time.

When detecting a peak based on a threshold from a given waveform, if many noise components are included, it is difficult to detect a peak. This is because detection based on the threshold pays attention to the root side of a peak. If noise components are superimposed, a portion which does not originally exceed the threshold and does not correspond to a peak exceeds the threshold, causing erroneous detection. To avoid such situation, paying attention to the tip side of a peak is effective. That is, even if a waveform includes many noise components, it is possible to detect a peak by specifying a portion protruding more than its peripheral portion. To specify a portion protruding more than its peripheral portion, the above-described condition is imposed.

In the present invention, as the value M obtained from the sampling data sequence of the ECG waveform, the sampling data itself, the amount of change (first derivative value) of the sampling data, or the product of the sampling data and the amount of change (first derivative value) of the sampling data is used.

If the sampling data itself is used as the value M obtained from the sampling data sequence, the peak of the R or S wave is detected as the peak of a waveform derived from a heartbeat.

If the amount of change (first derivative value) of the sampling data is used as the value M obtained from the sampling data sequence, the peak of the amount of change of the sampling data caused by an abrupt change from the R wave to the S wave is detected as the peak of a waveform derived from a heartbeat. In the sampling data sequence of the ECG waveform, the first derivative value of the sampling data at given time K is obtained by subtracting sampling data at time (K−W) from sampling data at time (K+W) (W is, for example, 5 ms).

If the product of the amount of change (first derivative value) of the sampling data and the sampling data is used as the value M obtained from the sampling data sequence, a peak synergistically emphasized by multiplication is detected as the peak of a waveform derived from a heartbeat. The sampling data sequence of the ECG waveform and a data sequence obtained by calculating the derivative of the ECG waveform each include peak components of the same beating rhythm. If these data sequences are overlaid by shifting them by a given time width, the peak components are synchronized with each other. Therefore, by multiplying the data sequences under appropriate conditions, it is possible to emphasize the peak components derived from the heartbeats.

To calculate a product, the first derivative value of the sampling data at given time K is multiplied by sampling data at time (K−t) a predetermined time t before time K. The peak of the first derivative value appears about 10 to 12 ms after the peak of the R wave of the ECG waveform. Therefore, if the first derivative value is used, the predetermined time t is set to satisfy 10 ms≤t≤12 ms.

First Embodiment

Figure 2:
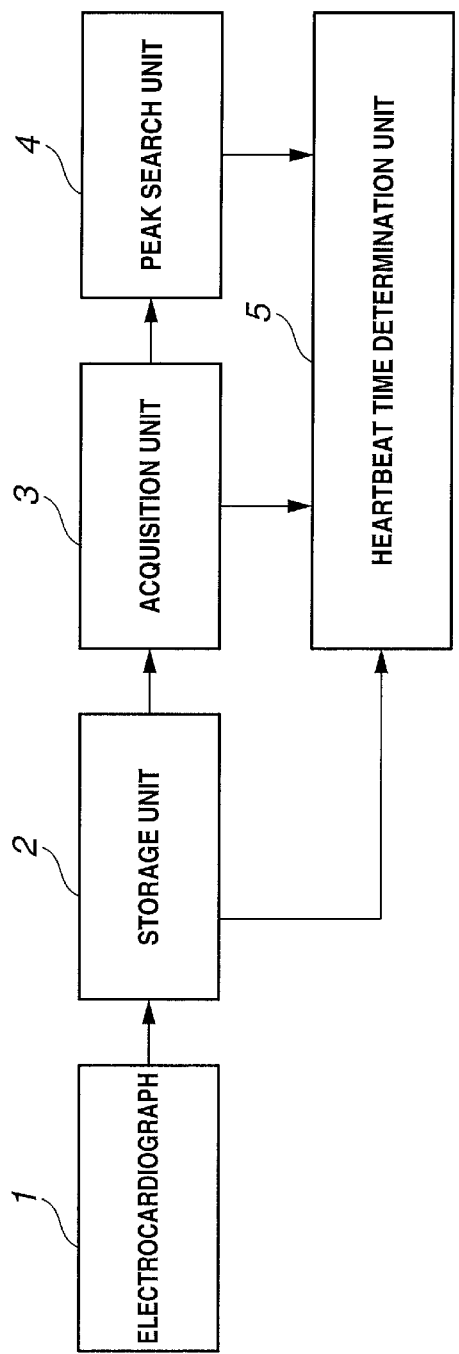
FIG. 2 is a block diagram showing the arrangement of a heartbeat detection device according the first embodiment of the present invention.
Figure 3:
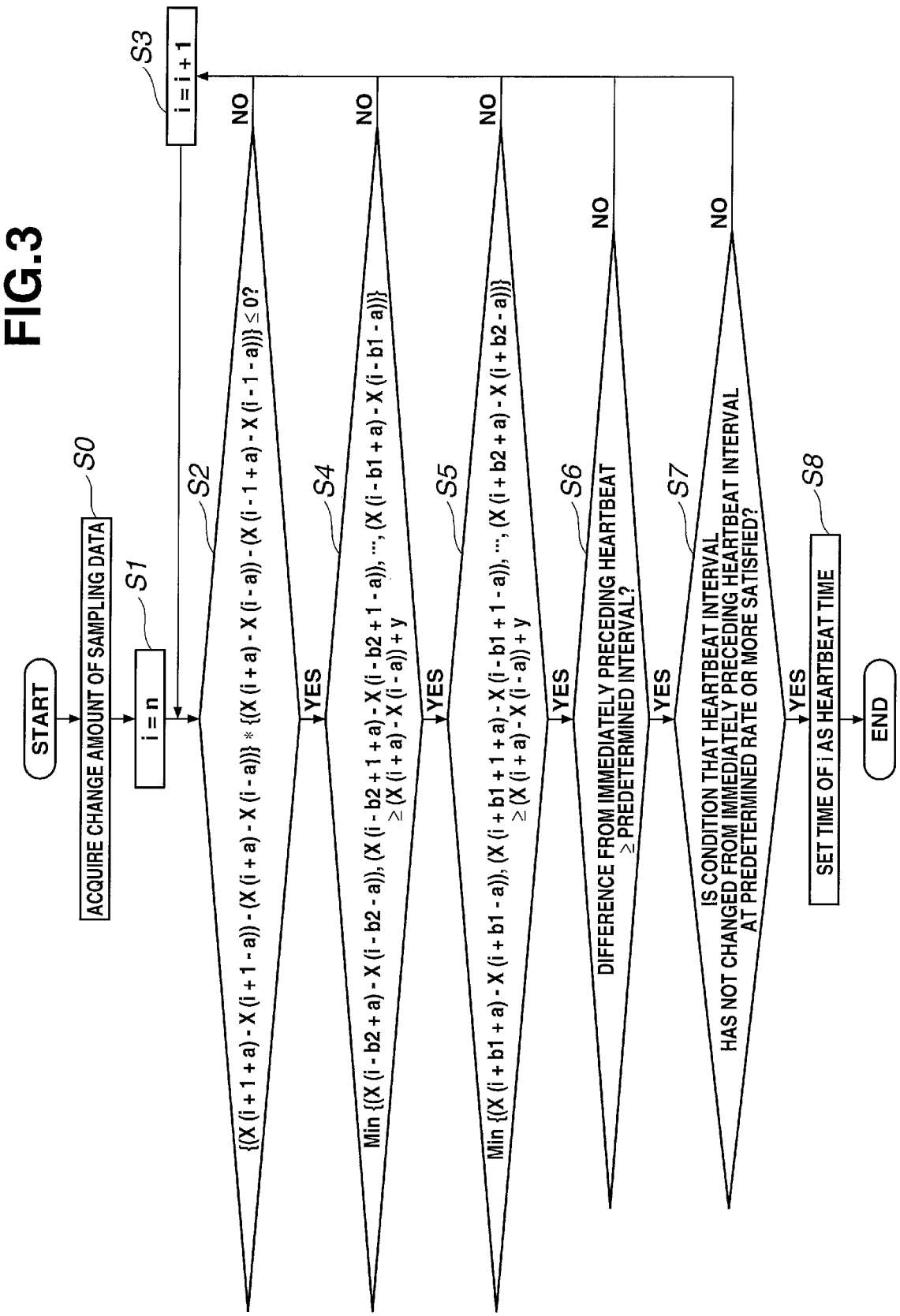
FIG. 3 is a flowchart for explaining a heartbeat detection method according to the first embodiment of the present invention.

An embodiment of the present invention will be described below with reference to the accompanying drawings. FIG. 2 is a block diagram showing the arrangement of a heartbeat detection device according to the first embodiment of the present invention. FIG. 3 is a flowchart for explaining a heartbeat detection method according to the first embodiment of the present invention. The heartbeat detection device includes an electrocardiograph 1, a storage unit 2, an acquisition unit 3 (acquisition means), a peak search unit 4 (peak search means), and a heartbeat time determination unit 5 (heartbeat time determination means).

The heartbeat detection method according to the embodiment will be described below. In this specification, a procedure of detecting a heartbeat and calculating heartbeat time of the heartbeat will be explained. By repeating calculation of heartbeat time for the period of ECG waveform data, sequential data of heartbeat times are successively obtained, and the index of a heartbeat fluctuation can be calculated from the sequential data.

In this embodiment, $X(i)$ represents a data sequence obtained by sampling the ECG waveform where i (i=1, 2, . . . ) represents a number assigned to one sampling data. As the number i is larger, sampling time is later, as a matter of course. Furthermore, a represents an integer obtained by dividing, by the sampling interval, half (W described above) the time interval when obtaining the first derivative value of the sampling data $X(i)$, b1 represents an integer obtained by dividing, by the sampling interval, first time ($\Delta t1$ described above) defining one of times defining the ends of a predetermined time domain around a peak, which is closer to the peak, and b2 represents an integer obtained by dividing, by the sampling interval, second time ($\Delta t2$ described above) defining the other one of times defining the ends of the predetermined time domain around the peak, which is farther from the peak (b2>b1).

The electrocardiograph 1 measures the ECG waveform of a living body (human body) (not shown), and outputs the sampling data sequence $X(i)$ of the ECG waveform. At this time, the electrocardiograph 1 outputs the data sequence by adding sampling time information to each sampling data. Note that a practical method of measuring the ECG waveform is a well-known technique and a detailed description thereof will be omitted.

The storage unit 2 stores the sampling data sequence $X(i)$ of the ECG waveform and the sampling time information, which have been output from the electrocardiograph 1.

The acquisition unit 3 acquires the amount of change of the sampling data $X(i)$ as a value M obtained from the sampling data sequence (step S0 of FIG. 3). More specifically, the acquisition unit 3 includes a calculation means (not shown). The calculation means calculates the amount of change of the sampling data $X(i)$, that is, a first derivative value $(X(i+a)-X(i-a))$ for each sampling time.

The peak search unit 4 searches for a peak at which the amount of change of the sampling data $X(i)$ changes from a decrease to an increase. First, the peak search unit 4 sets the number (counter variable) i for successively reading out the sampling data sequence $X(i)$ to an initial value (n in this example) (step S1 of FIG. 3).

Next, the peak search unit 4 determines whether $\{(X(i+1+a)-X(i+1-a))-(X(i+a)-X(i-a))\}\times\{(X(i+a)-X(i-a))-(X(i-1+a)-X(i-1-a))\}$ is equal to or smaller than 0 (step S2 of FIG. 3). $(X(i+1+a)-X(i+1-a))$ represents the amount of change of the sampling data $X(i+1)$ one sampling after the sampling data $X(i)$, and $(X(i-1+a)-X(i-1-a))$ represents the amount of change of the sampling data $X(i-1)$ one sampling before the sampling data $X(i)$.

If $\{(X(i+1+a)-X(i+1-a))-(X(i+a)-X(i-a))\}\times\{(X(i+a)-X(i-a))-(X(i-1+a)-X(i-1-a))\}$ is larger than 0, the peak search unit 4 determines that the amount of change of the sampling data $X(i)$ has not changed from a decrease to an increase, and sets i=i+(step S3 of FIG. 3), thereby returning to step S2. The processes in steps S2 and S3 are repeated until $\{(X(i+1+a)-X(i+1-a))-(X(i+a)-X(i-a))\}\times\{(X(i+a)-X(i-a))-(X(i-1+a)-X(i-1-a))\}$ becomes equal to or smaller than 0.

If $\{(X(i+1+a)-X(i+1-a))-(X(i+a)-X(i-a))\}\times\{(X(i+a)-X(i-a))-(X(i-1+a)-X(i-1-a))\}$ is equal to or smaller than 0, the peak search unit 4 determines that the amount of change of the sampling data $X(i)$ has changed from a decrease to an increase at time T indicated by i (YES in step S2).

If it is determined that the amount of change of the sampling data $X(i)$ has changed from a decrease to an increase, the heartbeat time determination unit 5 checks the amount of change of the sampling data in a time domain around time T indicated by i, and determines whether time T indicated by i is set as a heartbeat time.

First, the heartbeat time determination unit 5 obtains the minimum value of the amount of changes $\{(X(i-b2+a)-X(i-b2-a)), (X(i-b2+1+a)-X(i-b2+1-a)), \ldots, (X(i-b1+a)-X(i-b1-a))\}$ of the sampling data in a predetermined time domain before time T indicated by i, and determines whether this minimum value is equal to or larger than a value obtained by adding a predetermined amount y to the amount of change $(X(i+a)-X(i-a))$ of the sampling data $X(i)$ at time T indicated by i (step S4 of FIG. 3).

If the minimum value obtained in step S4 is smaller than $(X(i+a)-X(i-a))+y$, the heartbeat time determination unit 5 determines that the difference between the amount of change of the sampling data in the predetermined time domain before time T indicated by i and the amount of change (X(i+a)−X(i−a)) of the sampling data X(i) at time T indicated by i is smaller than the predetermined amount y, and sets i=i+1 (step S3), thereby returning to step S2.

On the other hand, if the minimum value obtained in step S4 is equal to or larger than (X(i+a)−X(i−a))+y, the heartbeat time determination unit 5 obtains the minimum value of the amount of changes {(X(i+b1+a)−X(i+b1−a)), (X(i+b1+1+a)−X(i+b1+1−a)), . . . , (X(i+b2+a)−X(i+b2−a))} of the sampling data in a predetermined time domain after time T indicated by i, and determines whether the minimum value is equal to or larger than a value obtained by adding the predetermined amount y to the amount of change (X(i+a)−X(i−a)) of the sampling data X(i) at time T indicated by i (step S5 of FIG. 3).

If the minimum value obtained in step S5 is smaller than (X(i+a)−X(i−a))+y, the heartbeat time determination unit 5 determines that the difference between the amount of change of the sampling data in the predetermined time domain after time T indicated by i and the amount of change (X(i+a)−X(i−a)) of the sampling data X(i) at time T indicated by i is smaller than the predetermined amount y, and sets i=i+1 (step S3), thereby returning to step S2.

If the minimum value obtained in step S5 is equal to or larger than (X(i+a)−X(i−a))+y, the heartbeat time determination unit 5 ends the processing of checking the amount of changes of the sampling data in the time domains around time T indicated by i. At this time, time T indicated by i is set as a candidate of heartbeat time.

Next, the heartbeat time determination unit 5 determines whether the candidate of heartbeat time is appropriate, and fixes heartbeat time.

First, the heartbeat time determination unit 5 determines whether the difference between time T indicated by i and immediately precedingly detected heartbeat time $T_{(-1)}$ is equal to or longer than a predetermined time (step S6 of FIG. 3). If the difference between time T and immediately preceding heartbeat time $T_{(-1)}$ is shorter than the predetermined time, the heartbeat time determination unit 5 discards time T indicated by i without adopting it as a heartbeat time, and returns to step S3.

A general normal value range exists for a heartbeat interval. If a very short heartbeat interval, as compared with the range, is detected, noise superimposed on an ECG waveform due to a body motion or the like is erroneously recognized as a heartbeat at high probability. It is possible to prevent erroneous detection caused by noise or the like by imposing the condition that the difference between time T of the detected peak and an immediately preceding heartbeat time $T_{(-1)}$ is equal to or longer than the predetermined time.

Furthermore, the heartbeat time determination unit 5 determines whether a heartbeat interval $(T-T_{(-1)})$ when time T indicated by i is considered as a heartbeat time has not increased from an immediately preceding heartbeat interval $(T_{(-1)}-T_{(-2)})$ at a predetermined rate or more (step S7 of FIG. 3). If the increasing rate $(T-T_{(-1)})/(T_{(-1)}-T_{(-2)})$ of the heartbeat interval is equal to or higher than a predetermined value, the heartbeat time determination unit 5 determines that the heartbeat interval has increased at the predetermined rate or more, and discards time T indicated by i without adopting it as a heartbeat time, thereby returning to step S3.

If detection of a given heartbeat fails, data obtained as the heartbeat interval between heartbeats before and after the given heartbeat indicates a value about twice larger than an actual value, and is inappropriately used for evaluation of the autonomic function or the like. It is possible to exclude the erroneous data, for which detection of a heartbeat has failed, from the analysis target of the biological information by imposing the condition that the detected heartbeat interval has not increased at the predetermined rate or more.

If the difference between time T indicated by i and an immediately preceding heartbeat time $T_{(-1)}$ is equal to or longer than the predetermined time, and the increasing rate $(T-T_{(-1)})/(T_{(-1)}-T_{(-2)})$ of the heartbeat interval is lower than the predetermined value, the heartbeat time determination unit 5 adopts time T indicated by i as a heartbeat time (step S8 of FIG. 3).

After the end of step S8, i=i+1 is set and the process returns to step S2. This starts detection of the next heartbeat. Alternatively, the values of i, the number of which corresponds to a predetermined time shorter than the minimum value of the heartbeat interval to be detected, may be skipped, and the process may returns to step S2. By repeating the processes in steps S2 to S8, it is possible to obtain the sequential data of the heartbeat times, and obtain the index of a heartbeat fluctuation from the sequential data.

Figure 4:
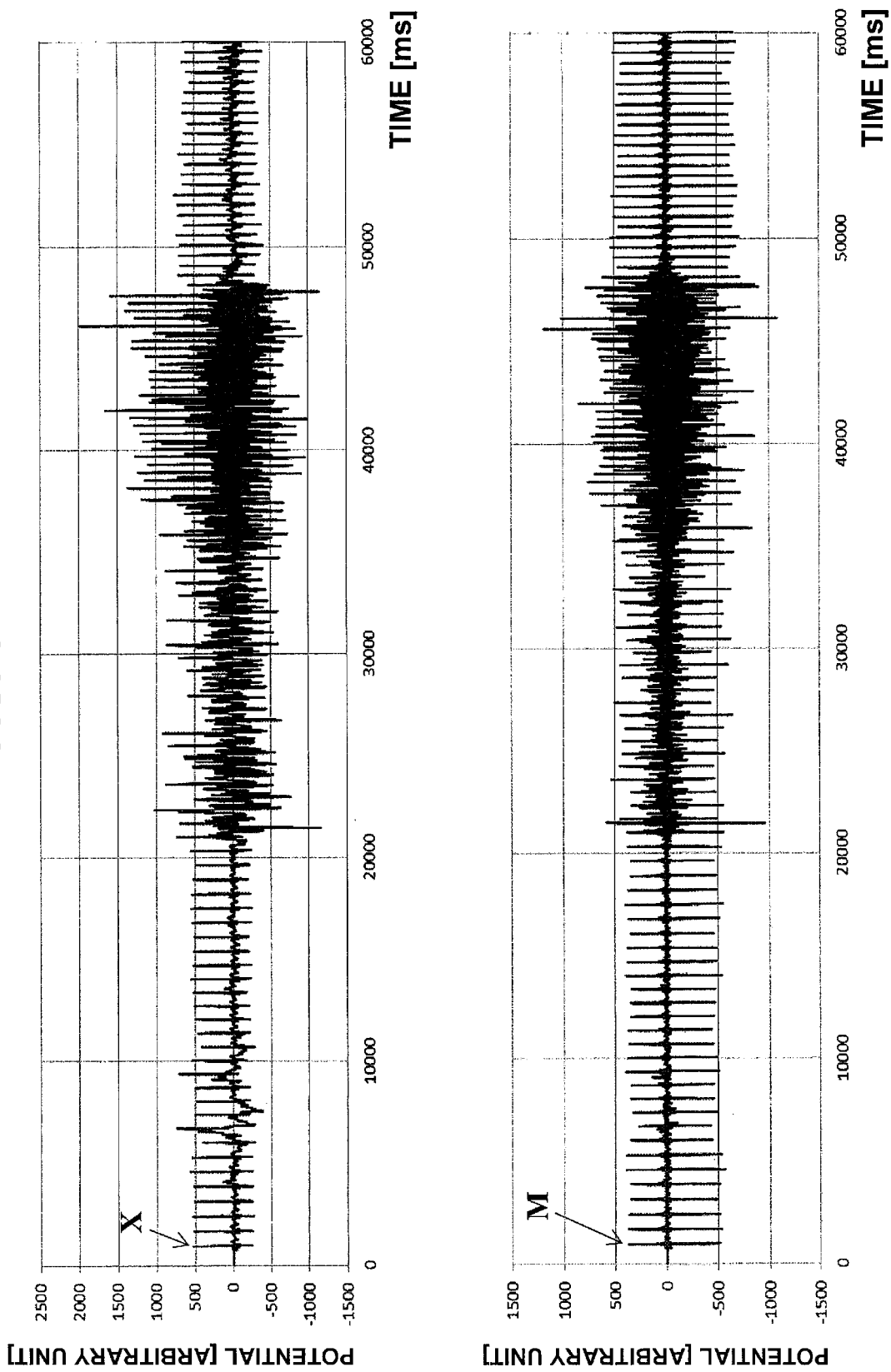
FIG. 4 shows graphs of an electrocardiographic waveform and the first derivative value of the electrocardiographic waveform.
Figure 5:
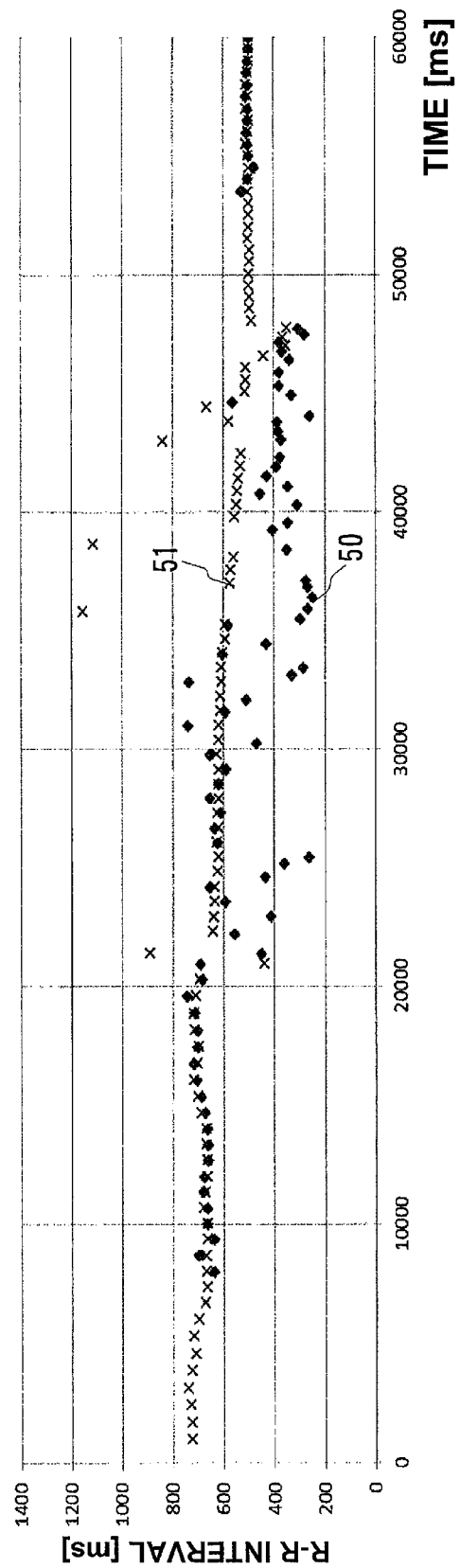
FIG. 5 is a graph showing R-R intervals obtained by the heartbeat detection methods according to the conventional technique and the first embodiment of the present invention.

FIGS. 4 and 5 show graphs for explaining the effect of this embodiment, and show an example in which R-R intervals are obtained from an ECG waveform. In FIG. 4, X represents an example of the sampling data of the ECG waveform, and M represents the first derivative value of the sampling data X. In FIG. 4, the abscissa represents the time [ms] and the ordinate represents the electric potential [arbitrary unit] replaced by a digital value. In FIG. 4, however, noise is added to the ECG waveform by a method in which, for example, a person to be measured runs during a period of 20,000 ms to 50,000 ms. It is found that although the first derivative values M include peaks of heartbeats, they are influenced by noise during the period of 20,000 ms to 50,000 ms.

FIG. 5 is a graph obtained by plotting R-R intervals (intervals between heartbeat times) obtained for the ECG waveform shown in FIG. 4 by the methods according to the conventional technique and this embodiment. The abscissa represents the time [ms] and the ordinate represents the R-R interval [ms]. A ♦ mark 50 in FIG. 5 indicates the R-R interval obtained by the conventional technique, and a × mark 51 indicates the R-R interval obtained by the method according to this embodiment. As the conventional technique, a method complying with the literature "ECG Implementation on the TMS320C5515 DSP Medical Development Kit (MDK) with the ADS1298 ECG-FE", Texas Instruments Incorporated, <http://www.ti.com/lit/an/sprabj1/sprabj1.pdf>, 2011 is used. It is considered that correct R-R intervals exist around 700 ms to 500 ms. In the conventional technique, however, there are many failures of heartbeat detection in a section during which noise is added to the ECG waveform. On the other hand, in this embodiment, it is understood that there are a few failures of heartbeat detection even in the section during which noise is added to the ECG waveform.

As described above, in this embodiment, it is possible to appropriately detect a heartbeat even from a sampling data sequence including noise by detecting a peak derived from a heartbeat based on the tip portion of the peak in the sampling data sequence of the ECG waveform. In this embodiment, since a peak derived from a heartbeat is detected without using a threshold, even if the level of a target ECG waveform changes, it is possible to appropriately detect the heartbeat without any influence of the change.

Second Embodiment

Figure 6:
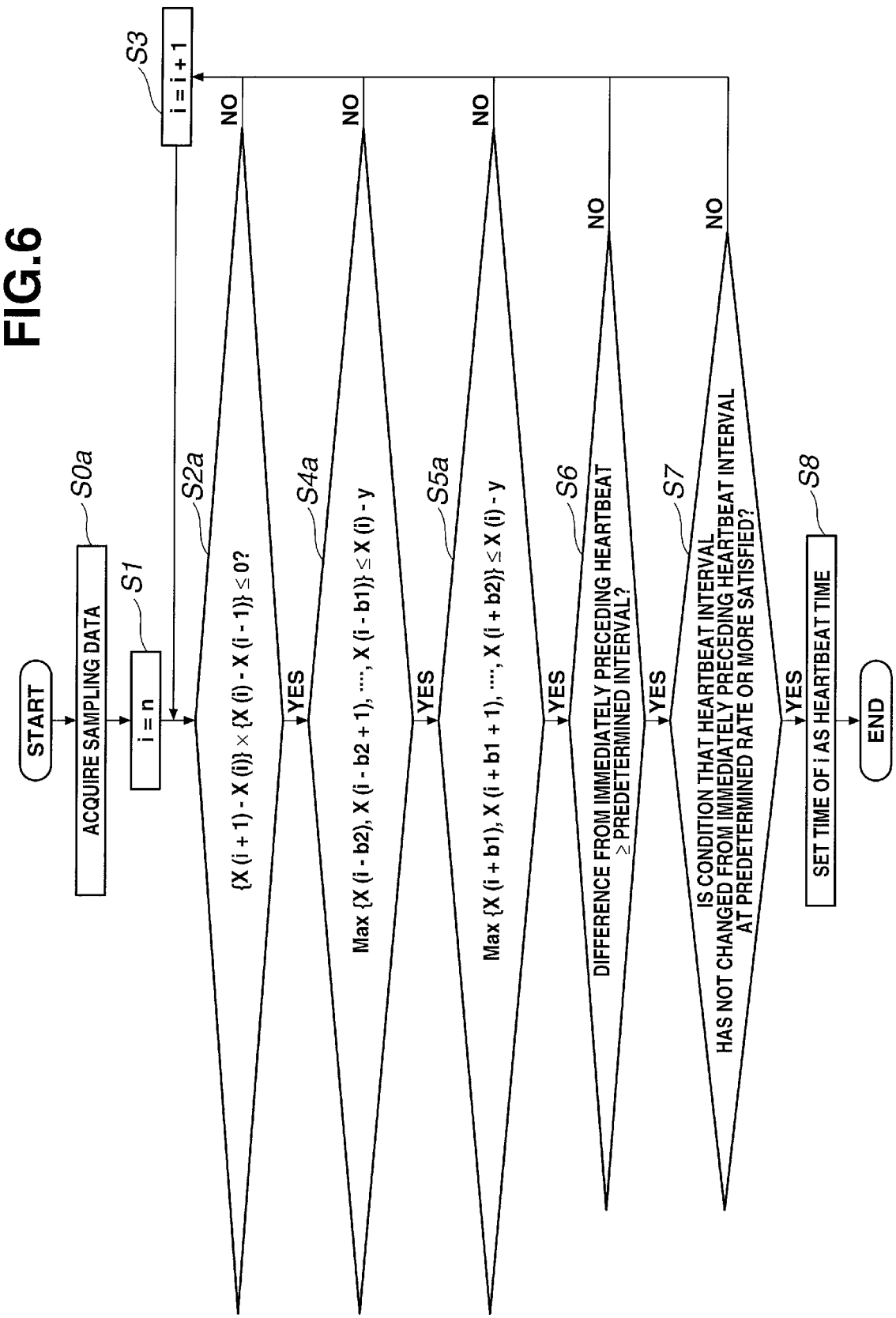
FIG. 6 is a flowchart for explaining a heartbeat detection method according to the second embodiment of the present invention.

The second embodiment of the present invention will be described next. This embodiment is a modification of the first embodiment, and is an example in which sampling data itself is used as a value M obtained from a sampling data sequence. In this embodiment, the arrangement of a heartbeat detection device is the same as in the first embodiment, and a description thereof will be provided using reference numerals in FIG. 2. FIG. 6 is a flowchart for explaining a heartbeat detection method according to this embodiment.

An acquisition unit 3 according to this embodiment acquires, from a storage unit 2, sampling data X(i) as the value M obtained from the sampling data sequence (step S0a of FIG. 6).

A peak search unit 4 determines whether {X(i+1)−X(i)}×{X(i)−X(i−1)} is equal to or smaller than 0 (step S2a of FIG. 6). If {X(i+1)−X(i)}×{X(i)−X(i−1)} is equal to or smaller than 0, the peak search unit 4 determines that the sampling data X(i) changes from an increase to a decrease at time T indicated by i (YES in step S2a).

If it is determined that the sampling data X(i) changes from an increase to a decrease, a heartbeat time determination unit 5 obtains the maximum value of sampling data {X(i−b2), X(i−b2+1), . . . , X(i−b1)} of a predetermined time domain before time T indicated by i, and determines whether the maximum value is equal to or smaller than a value obtained by subtracting a predetermined amount y from the sampling data X(i) at time T indicated by i (step S4a of FIG. 6). If the maximum value obtained in step S4a is larger than X(i)−y, the heartbeat time determination unit 5 determines that the difference between the sampling data in the predetermined time domain before time T indicated by i and the sampling data X(i) at time T indicated by i is smaller than the predetermined amount y, and sets i=i+1 (step S3), thereby returning to step S2a.

On the other hand, if the maximum value obtained in step S4a is equal to or smaller than X(i)−y, the heartbeat time determination unit 5 obtains the maximum value of sampling data {X(i+b1), X(i+b1+1), . . . , X(i+b2)} in a predetermined time domain after time T indicated by i, and determines whether the maximum value is equal to or smaller than the value obtained by subtracting the predetermined amount y from the sampling data X(i) at time T indicated by i (step S5a of FIG. 6). If the maximum value obtained in step S5a is larger than X(i)−y, the heartbeat time determination unit 5 determines whether the difference between the sampling data in the predetermined time domain after time T indicated by i and the sampling data X(i) at time T indicated by i is smaller than the predetermined amount y, and sets i=i+1 (step S3), thereby returning to step S2a.

If the maximum value obtained in step S5a is equal to or smaller than X(i)−y, the heartbeat time determination unit 5 ends the processing of checking the sampling data in the time domains around time T indicated by i. The remaining arrangement is as described in the first embodiment.

Figure 7:
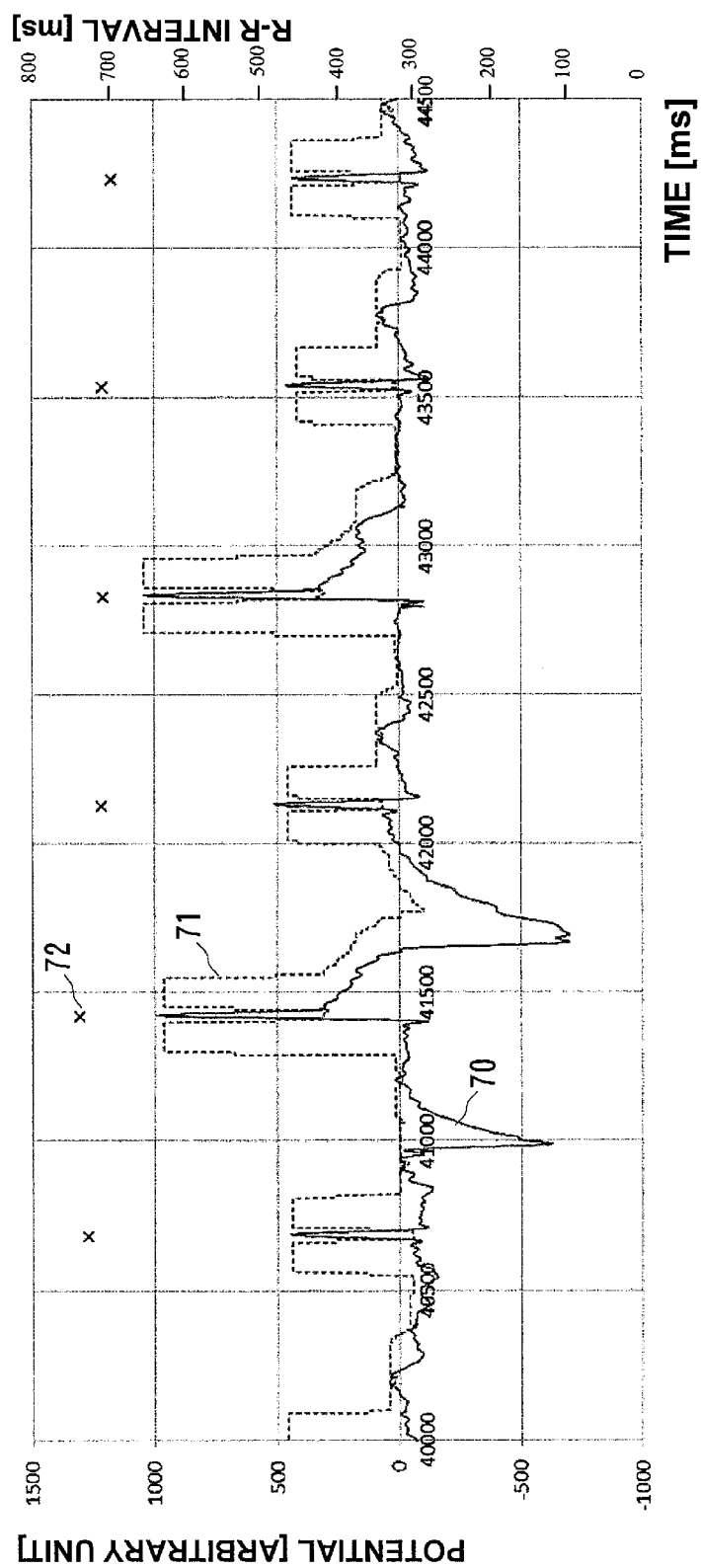
FIG. 7 is a graph showing an electrocardiographic waveform, the maximum values of the sampling values of the electrocardiographic waveform, and R-R intervals obtained by a heartbeat detection method according to the second embodiment of the present invention.

FIG. 7 is a graph for explaining an operation according to this embodiment. To obtain an R-R interval from an ECG waveform, the upward convex peak of the R wave is detected. A solid line 70 in FIG. 7 indicates an ECG waveform. A broken line 71 is obtained as a result of plotting, for each time, at the position of time T, the maximum values of the sampling data in a predetermined time domain of (T−Δt2) to (T−Δt1) before time T and a predetermined time domain of (T+Δt1) to (T+Δt2) after time T. In this example, Δt1=25 ms and Δt2=125 ms.

In the example of FIG. 7, the original sampling data sequence has an interval of 1 ms. The maximum values indicated by the broken line 71 are calculated based on data extracted at an interval of 10 ms. The data sequence hardly includes spike-like abnormal values having a width smaller than a 10-ms width in addition to the original R waves. Therefore, it is possible to obtain a sufficiently effective function as a means for measuring a clearance while reducing the calculation load by coarsely obtaining data to be used to obtain the maximum values.

In this embodiment, with respect to time T of the peak at which the sampling data of the ECG waveform changes from an increase to a decrease, the sampling data in the predetermined time domain of (T−Δt2) to (T−Δt1) before time T of the peak and the sampling data in the predetermined time domain of (T+Δt1) to (T+Δt2) after time T of the peak are checked. If the differences between the sampling data at time T of the peak and the maximum values of the sampling data in the predetermined time domains are equal to or larger than the predetermined amount y, time T of the peak is set as a heartbeat time.

In FIG. 7, a value at time T of the peak at which the solid line 70 changes from an increase to a decrease is compared with a value indicated by the broken line 71 at time T. If the value of the solid line 70 is larger than the value of the broken line 71 by the predetermined amount y or more, time T of the peak is set as a heartbeat time. The R-R intervals (the intervals between heartbeat times) obtained from thus detected heartbeat times are indicated by x marks 72 in FIG. 7. In this example, y=100.

As described above, in this embodiment, it is possible to obtain the same effect as in the first embodiment.

Third Embodiment

Figure 8:
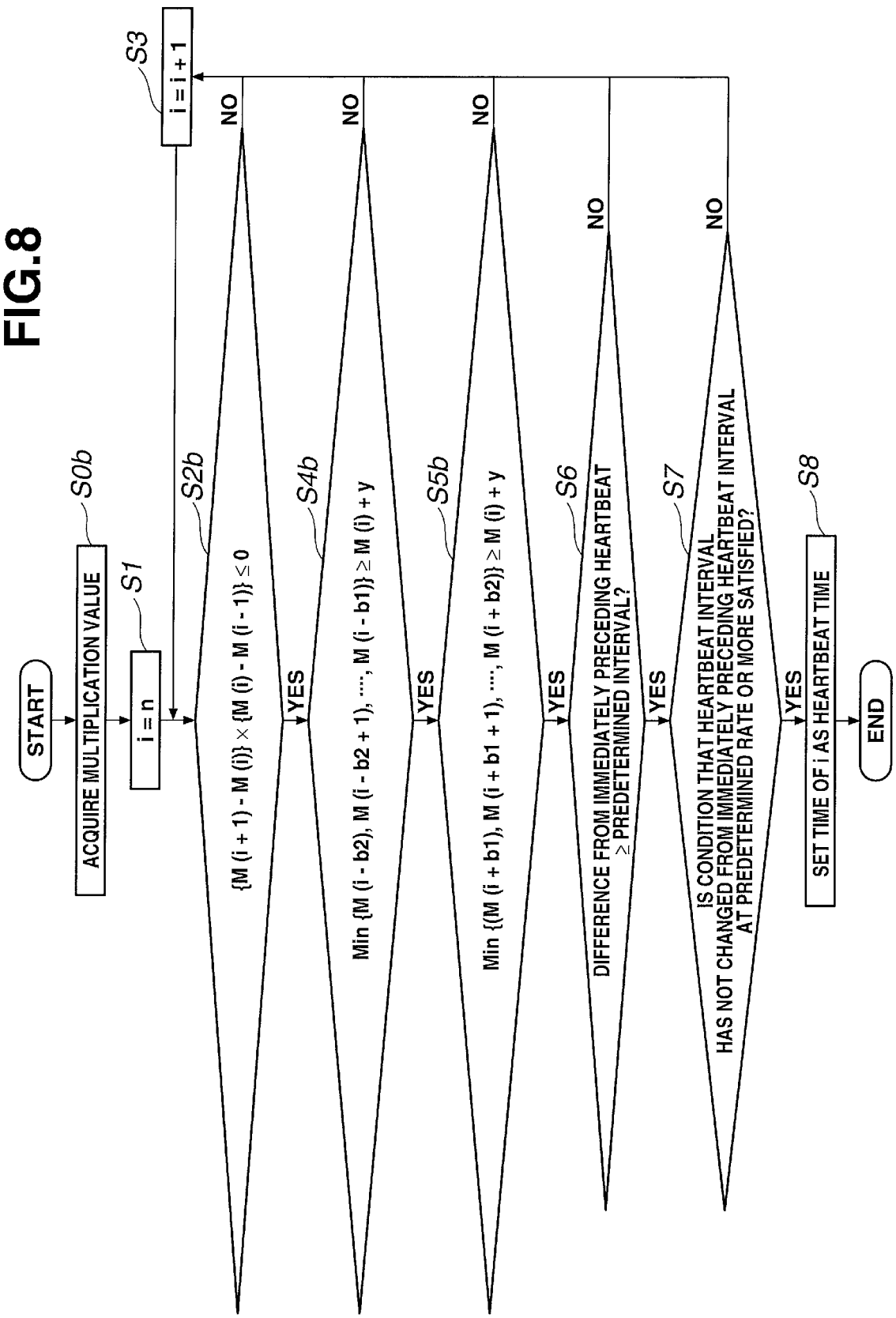
FIG. 8 is a flowchart for explaining a heartbeat detection method according to the third embodiment of the present invention.

The third embodiment of the present invention will be described next. This embodiment is a modification of the first embodiment, and is an example in which the product of sampling data and the amount of change (first derivative value) of sampling data is used as a value M obtained from a sampling data sequence. In this embodiment as well, the arrangement of a heartbeat detection device is the same as in the first embodiment, and a description thereof will be provided using reference numerals in FIG. 2. FIG. 8 is a flowchart for explaining a heartbeat detection method according to this embodiment.

An acquisition unit 3 according to this embodiment acquires, as the value M obtained from the sampling data sequence, the product of sampling data and the amount of change (first derivative value) of sampling data (step S0b of FIG. 8). More specifically, the acquisition unit 3 includes a calculation means (not shown). The calculation means calculates, for each sampling time, a first derivative value (X(i+a)−X(i−a)) of sampling data X(i), and also calculates, for each sampling time, a product (X(i+a)−X(i−a))×X(i−b) of the first derivative value (X(i+a)−X(i−a)) of the sampling data X(i) and sampling data X(i−b) at time a predetermined time t before the sampling data X(i). In this example, b represents an integer obtained by dividing the predetermined time t by the sampling interval. As described above, the predetermined time t is set to satisfy 10 ms≤t≤12 ms.

The following description assumes that the product (X(i+a)−X(i−a))×X(i−b) is set as M(i).

A peak search unit 4 determines whether {M(i+1)−M(i)}×{M(i)−M(i−1)} is equal to or smaller than 0 (step S2b of FIG. 8). M(i+1) represents a product one sampling after the sampling data X(i), and M(i−1) represents a product one sampling before the sampling data X(i). If {M(i+1)−M(i)}×{M(i)−M(i−1)} is equal to or smaller than 0, the peak search unit 4 determines that the product M(i) changes from a decrease to an increase at time T indicated by i (YES in step S2b).

If it is determined that the product M(i) changes from a decrease to an increase, a heartbeat time determination unit 5 obtains the minimum value of products {M(i−b2), M(i−b2+1), . . . , M(i−b1)} in a predetermined time domain before time T indicated by i, and determines whether the minimum value is equal to or larger than a value obtained by adding a predetermined amount y to the product M(i) at time T indicated by i (step S4b of FIG. 8). If the minimum value obtained in step S4b is smaller than M(i)+y, the heartbeat time determination unit 5 determines that the difference between the product in the predetermined time domain before time T indicated by i and the product M(i) at time T indicated by i is smaller than the predetermined amount y, and sets i=i+1 (step S3), thereby returning to step S2b.

On the other hand, if the minimum value obtained in step S4b is equal to or larger than M(i)+y, the heartbeat time determination unit 5 obtains the minimum value of products {M(i+b1), M(i+b1+1), . . . , M(i+b2)} in a predetermined time domain after time T indicated by i, and determines whether the minimum value is equal to or larger than the value obtained by adding the predetermined amount y to the product M(i) at time T indicated by i (step S5b of FIG. 8). If the minimum value obtained in step S5b is smaller than M(i)+y, the heartbeat time determination unit 5 determines that the difference between the product in the predetermined time domain after time T indicated by i and the product M(i) at time T indicated by i is smaller than the predetermined amount y, and sets i=i+1 (step S3), thereby returning to step S2b.

If the minimum value obtained in step S5b is equal to or larger than M(i)+y, the heartbeat time determination unit 5 ends the processing of checking the products in the time domains around time T indicated by i. The remaining arrangement is as described in the first embodiment.

Figure 9:
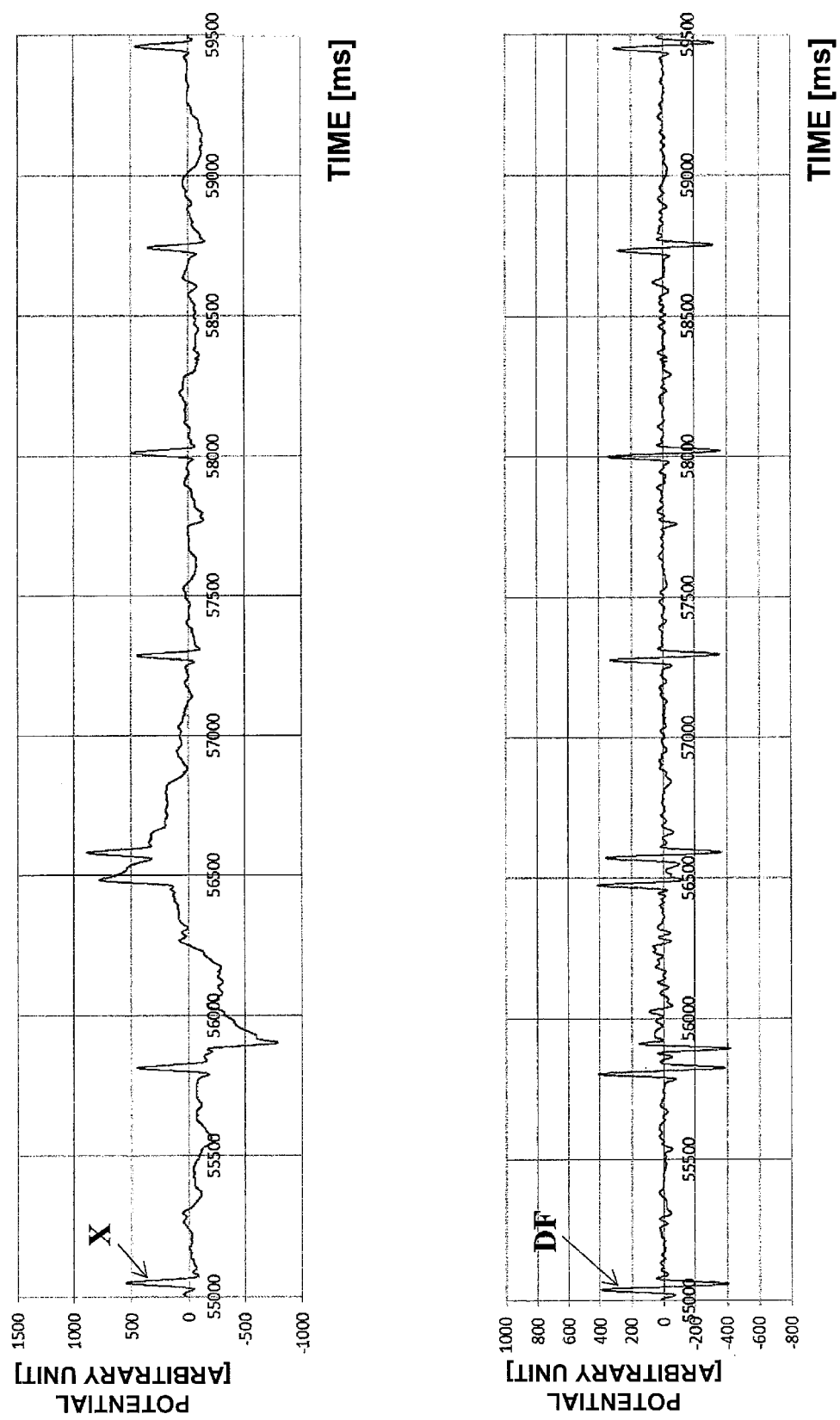
FIG. 9 shows graphs of an electrocardiographic waveform and the first derivative value of the electrocardiographic waveform.
Figure 10:
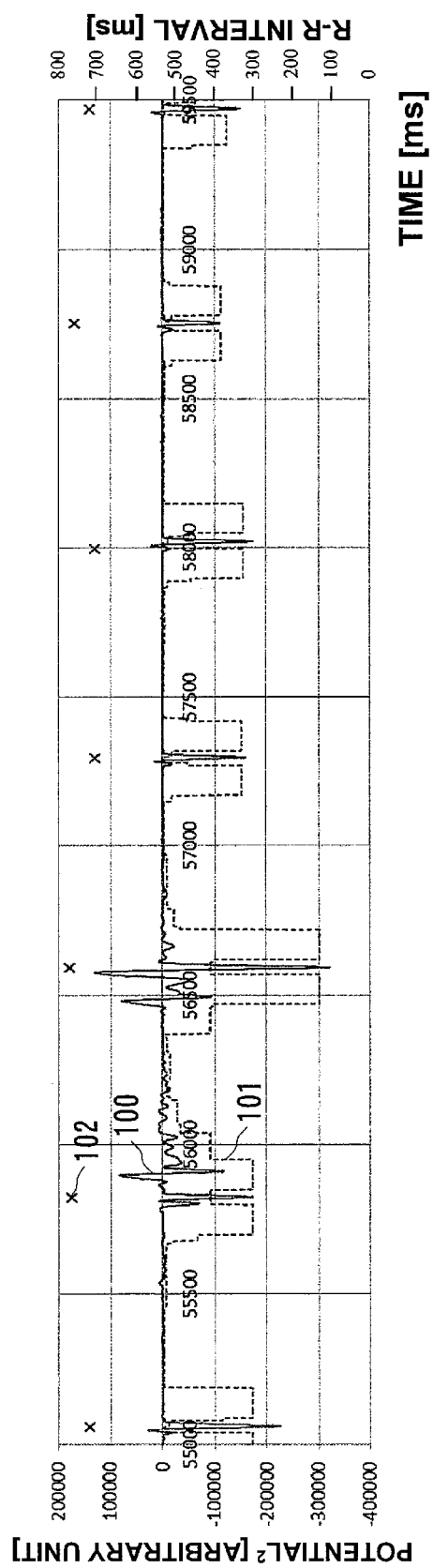
FIG. 10 is a graph showing a product obtained by multiplying the first derivative value of the electrocardiographic waveform by an electrocardiographic waveform.
Figure 11:
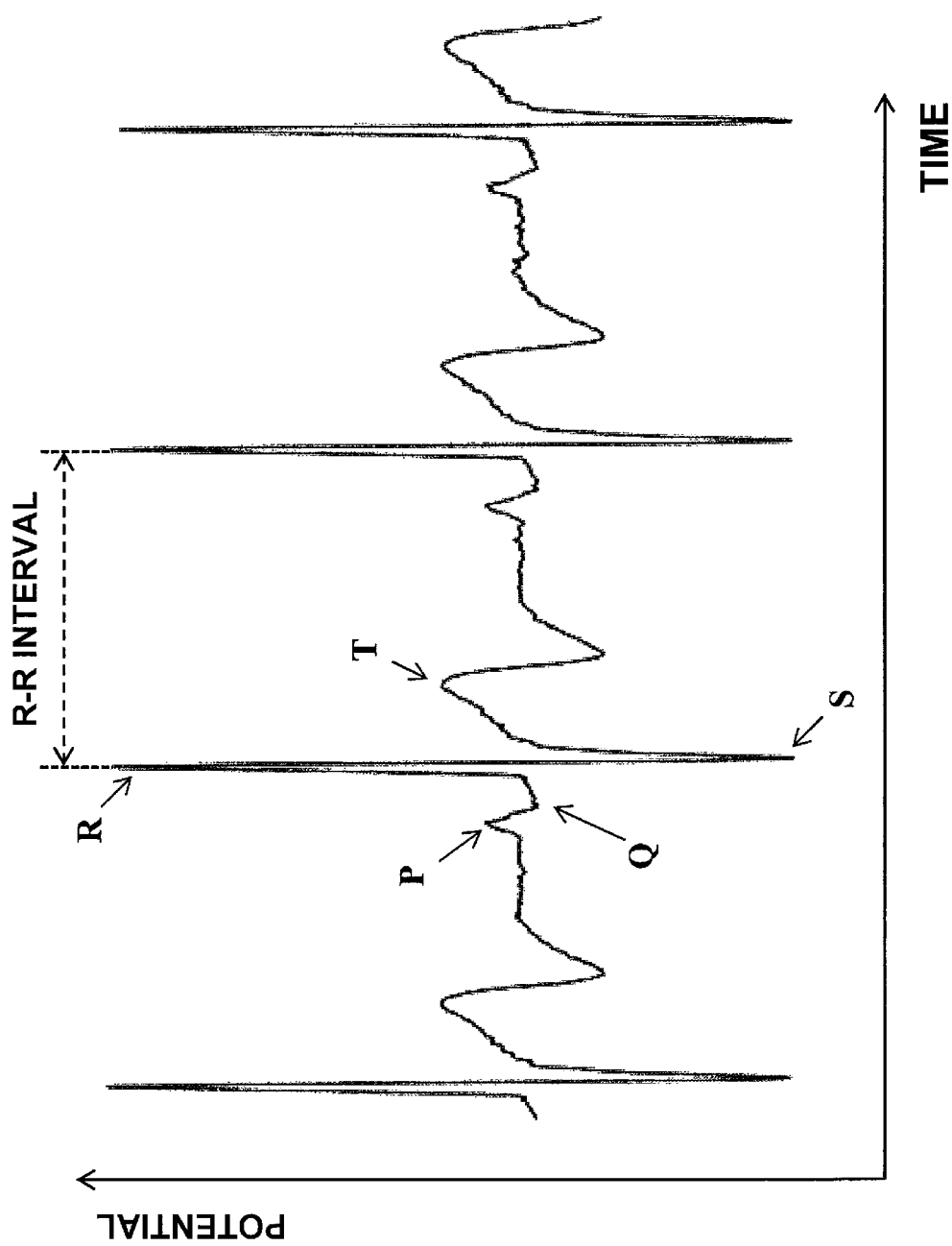
FIG. 11 is a graph showing an example of an electrocardiographic waveform.
Figure 12:
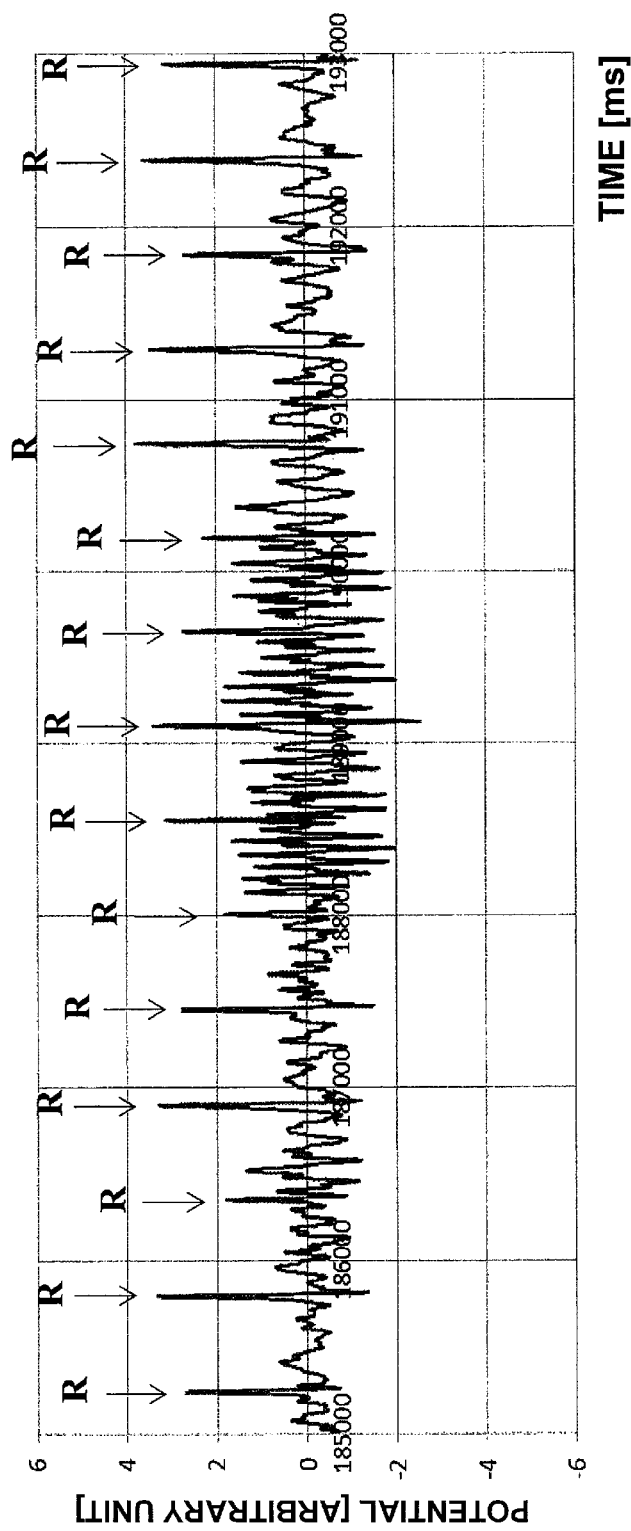
FIG. 12 is a graph for explaining the conventional problem.

FIGS. 9 and 10 show graphs for explaining an operation according to this embodiment. In FIG. 9, X represents an example of the sampling data of an ECG waveform, and DF represents the first derivative value of the sampling data X. A solid line 100 in FIG. 10 indicates the product M obtained by multiplying the first derivative value DF of the sampling data X in FIG. 9 by the sampling data X 10 ms before. The ordinate in FIG. 10 represents the square [arbitrary unit] of the electric potential.

The R and S waves of the ECG waveform are generated by ventricular contraction, and the interval from the peak of the R wave of the ECG waveform to the peak of the first derivative value caused by an abrupt decrease in potential from the R wave to the S wave is about 10 ms, and is hardly influenced by a body type difference or the like. In this case, since the downward convex peak of the first derivative value of the ECG waveform is multiplied by the upward convex peak of the R wave of the ECG waveform, a peak to be detected to obtain an R-R interval is a downward convex peak.

A broken line 101 in FIG. 10 is obtained as a result of plotting, for each time, at the position of time T, the minimum values of the products M in a predetermined time domain of (T−Δt2) to (T−Δt1) before time T and a predetermined time domain of (T+Δt1) to (T+Δt2) after time T. In this example, Δt1=25 ms and Δt2=125 ms. Similarly to the example of FIG. 7, in the example of FIG. 10, the original products M have an interval of 1 ms but the minimum values indicated by the broken line 101 are calculated based on data extracted at an interval of 10 ms.

In this embodiment, with respect to time T of the peak at which the product M changes from a decrease to an increase, the product M in the predetermined time domain of (T−Δt2) to (T−Δt1) before time T of the peak and the product M in the predetermined time domain of (T+Δt1) to (T+Δt2) after time T of the peak are checked. If the differences between the product M at time T of the peak and the minimum values of the products M in the predetermined time domains are equal to or larger than the predetermined amount y, time T of the peak is set as a heartbeat time.

In FIG. 10, a value at time T of the peak at which the solid line 100 changes from a decrease to an increase is compared with a value indicated by the broken line 101 at time T. If the value of the solid line 100 is smaller than the value of the broken line 101 by the predetermined amount y or more, time T of the peak is set as a heartbeat time. The R-R intervals (the intervals between heartbeat times) obtained from thus detected heartbeat times are indicated by × marks 102 in FIG. 10. In this example, y=10,000.

As described above, in this embodiment, it is possible to obtain the same effect as in the first embodiment.

It is possible to obtain a significant effect by applying the heartbeat detection method according to each of the first to third embodiments to the ECG waveform of the ECG lead in which a large R wave and a deep S wave are obtained, for example, the ECG waveform of one of the V3 to V5 leads. It is especially preferable to apply the method to the ECG waveform of the CC5 lead or similar lead which is often used to obtain the ECG waveform in daily life.

The storage unit 2, acquisition unit 3, peak search unit 4, and heartbeat time determination unit 5 described in each of the first to third embodiments can be implemented by a computer including a CPU (Central Processing Unit), storage device, and interface and a program that controls these hardware resources. The CPU executes the processing described in each of the first to third embodiments in accordance with the program stored in the storage device.

INDUSTRIAL APPLICABILITY

The present invention is applicable to a technique of detecting heartbeats of a living body.

EXPLANATION OF THE REFERENCE NUMERALS AND SIGNS

1 . . . electrocardiograph, 2 . . . storage unit, 3 . . . acquisition unit, 4 . . . peak search unit, 5 . . . heartbeat time determination unit

The invention claimed is:

1. A heartbeat detection method comprising:
a peak search step of searching for one of a peak at which values M obtained from a sequence of sampling data of an electrocardiographic waveform of a living body change from an increase to a decrease and a peak at which the values M change from a decrease to an increase, wherein each of the values M includes an amount of change of the sampling data, or, a product of the sampling data and the amount of change of the sampling data;
a heartbeat time determination step of checking among the values M obtained from the sequence of sampling data, values M in a predetermined time domain before a time of the peak and values M in a predetermined time domain after the time of the peak, and setting the time of the peak as a heartbeat time if differences between a value M at the time of the peak and the values M in the predetermined time domains are not smaller than a predetermined amount, wherein the value M and each of the values M include the amount of change of the sampling data, or, the product of the sampling data and the amount of change of the sampling data;

generating sequence data to calculate adjusted heartbeat times from the obtained heartbeat times by repeating the peak search step and the heartbeat time determination step; and using the adjusted heartbeat times to generate an ECG waveform to determine heartbeat fluctuations for said living body.

2. The heartbeat detection method according to claim 1, further comprising:

an acquisition step of acquiring, before the peak search step, as the values M obtained from the sequence of sampling data of the electrocardiographic waveform of the living body, one of the amount of change of the sampling data, and the product of the sampling data and the amount of change of the sampling data.

3. The heartbeat detection method according to claim 1, wherein the heartbeat time determination step includes determining whether a difference between the time of the peak and an immediately preceding heartbeat time which is a heartbeat time during an immediately preceding cycle is not shorter than a predetermined time, and not adopting the time of the peak as a heartbeat time if the difference is shorter than the predetermined time.

4. The heartbeat detection method according to claim 1, wherein the heartbeat time determination step includes determining whether a heartbeat interval when the time of the peak is considered as a heartbeat time has not increased from an immediately preceding heartbeat interval which is a heartbeat interval during an immediately preceding cycle at a rate not lower than a predetermined rate, and not adopting the time of the peak as a heartbeat time if the heartbeat interval has increased at the rate not lower than the predetermined rate.

5. A heartbeat detection device comprising:

peak search means for searching for one of a peak at which values M obtained from a sampling data sequence of an electrocardiographic waveform of a living body change from an increase to a decrease and a peak at which the values M change from a decrease to an increase, wherein each of the values M includes an amount of change of the sampling data, or, a product of the sampling data and the amount of change of the sampling data;

heartbeat time determination means for checking, among the values M obtained from the sampling data sequence, values M in a predetermined time domain before a time of the peak and values M in a predetermined time domain after the time of the peak, and setting the time of the peak as a heartbeat time if differences between a value M at the time of the peak and the values M in the predetermined time domains are not smaller than a predetermined amount, wherein the value M and each of the values M include the amount of change of the sampling data, or, the product of the sampling data and the amount of change of the sampling data;

sequence data generation means for calculating adjusted heartbeat times from the obtained heartbeat times by repeating processings by the peak search means and the heartbeat time determination means; and ECG waveform generation means for determining heartbeat fluctuations for said living body using the adjusted heartbeat times.

6. The heartbeat detection device according to claim 5, further comprising:

acquisition means for acquiring, as the values M obtained from the sampling data sequence of the electrocardiographic waveform of the living body, one of the amount of change of the sampling data, and the product of the sampling data and the amount of change of the sampling data.

7. The heartbeat detection device according to claim 5, wherein the heartbeat time determination means determines whether a difference between the time of the peak and an immediately preceding heartbeat time which is a heartbeat time during an immediately preceding cycle is not shorter than a predetermined time, and does not adopt the time of the peak as a heartbeat time if the difference is shorter than the predetermined time.

8. The heartbeat detection device according to claim 5, wherein the heartbeat time determination means determines whether a heartbeat interval when the time of the peak is considered as a heartbeat time has not increased from an immediately preceding heartbeat interval which is a heartbeat interval during an immediately preceding at a rate not lower than a predetermined rate, and does not adopt the time of the peak as a heartbeat time if the heartbeat interval has increased at the rate not lower than the predetermined rate.

9. A heartbeat detection method comprising:

a step of storing sampling time information and a sequence of sampling data of an electrocardiographic waveform of a living body, which have been output from an electrocardiograph;

a peak search step of searching for one of a peak at which values M obtained from the sequence of sampling data change from an increase to a decrease and a peak at which the values M change from a decrease to an increase;

a heartbeat time determination step of checking among the values M obtained from the sequence of sampling data without the sampling time information, values M in a predetermined time domain before a time of the peak and values M in a predetermined time domain after the time of the peak, and setting the time of the peak as a heartbeat time if differences between a value M at the time of the peak and the values M in the predetermined time domains are not smaller than a predetermined amount;

generating sequence data to calculate adjusted heartbeat times from the obtained heartbeat times by repeating the peak search step and the heartbeat time determination step; and using the adjusted heartbeat times to generate an ECG waveform to determine heartbeat fluctuations for said living body.

10. The heartbeat detection method according to claim 9, further comprising:

an acquisition step of acquiring, before the peak search step, as the values M obtained from the sequence of sampling data of the electrocardiographic waveform of the living body, one of the sampling data, an amount of change of the sampling data, and a product of the sampling data and the amount of change of the sampling data.

11. The heartbeat detection method according to claim 9, wherein the heartbeat time determination step includes determining whether a difference between the time of the peak and an immediately preceding heartbeat time which is a heartbeat time during an immediately preceding cycle is not shorter than a predetermined time, and not adopting the time of the peak as a heartbeat time if the difference is shorter than the predetermined time.

12. The heartbeat detection method according to claim 9, wherein the heartbeat time determination step includes determining whether a heartbeat interval when the time of the peak is considered as a heartbeat time has not increased from an immediately preceding heartbeat interval which is a heartbeat interval during an immediately preceding cycle at a rate not lower than a predetermined rate, and not adopting the time of the peak as a heartbeat time if the heartbeat interval has increased at the rate not lower than the predetermined rate.

13. A heartbeat detection device comprising:
   storage means for storing sampling time information and a sampling data sequence of an electrocardiographic waveform of a living body, which have been output from an electrocardiograph;
   peak search means for searching for one of a peak at which values M obtained from the sampling data sequence change from an increase to a decrease and a peak at which the values M change from a decrease to an increase;
   heartbeat time determination means for checking, among the values M obtained from the sampling data sequence without the sampling time information, values M in a predetermined time domain before a time of the peak and values M in a predetermined time domain after the time of the peak, and setting the time of the peak as a heartbeat time if differences between a value M at the time of the peak and the values M in the predetermined time domains are not smaller than a predetermined amount;
   sequence data generation means for calculating adjusted heartbeat times from the obtained heartbeat times by repeating processings by the peak search means and the heartbeat time determination means; and
   ECG waveform generation means for determining heartbeat fluctuations for said living body using the adjusted heartbeat times.

14. The heartbeat detection device according to claim 13, further comprising:
   acquisition means for acquiring, as the values M obtained from the sampling data sequence of the electrocardiographic waveform of the living body, one of the sampling data, an amount of change of the sampling data, and a product of the sampling data and the amount of change of the sampling data.

15. The heartbeat detection device according to claim 13, wherein the heartbeat time determination means determines whether a difference between the time of the peak and an immediately preceding heartbeat time which is a heartbeat time during an immediately preceding cycle is not shorter than a predetermined time, and does not adopt the time of the peak as a heartbeat time if the difference is shorter than the predetermined time.

16. The heartbeat detection device according to claim 13, wherein the heartbeat time determination means determines whether a heartbeat interval when the time of the peak is considered as a heartbeat time has not increased from an immediately preceding heartbeat interval which is a heartbeat interval during an immediately preceding at a rate not lower than a predetermined rate, and does not adopt the time of the peak as a heartbeat time if the heartbeat interval has increased at the rate not lower than the predetermined rate.

* * * * *